US006512096B2

(12) United States Patent
Weiner et al.

(10) Patent No.: US 6,512,096 B2
(45) Date of Patent: *Jan. 28, 2003

(54) PROSTATE CELL SURFACE ANTIGEN-SPECIFIC ANTIBODIES

(75) Inventors: George J. Weiner, Iowa City, IA (US); Oskar W. Rokhlin, Coralville, IA (US); Michael B. Cohen, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/757,336

(22) Filed: Jan. 9, 2001

(65) Prior Publication Data

US 2001/0001310 A1 May 17, 2001

Related U.S. Application Data

(63) Continuation of application No. 09/104,717, filed on Jun. 25, 1998, now Pat. No. 6,207,805, which is a continuation-in-part of application No. 08/896,447, filed on Jul. 18, 1997, now abandoned.

(51) Int. Cl.[7] ............................................. A61K 34/395
(52) U.S. Cl. .............................. 530/388.85; 530/387.3; 530/388.1; 530/391.7
(58) Field of Search .......................... 530/388.1, 388.8, 530/388.85, 391.3, 391.7, 387.1, 387.3; 435/188, 326; 424/178.1, 156.1, 133.1

(56) References Cited

U.S. PATENT DOCUMENTS

| 4,474,893 | A | * | 10/1984 | Reading |
|---|---|---|---|---|
| 4,671,958 | A | | 6/1987 | Rodwell et al. |
| 4,699,784 | A | | 10/1987 | Shih et al. |
| 4,722,899 | A | * | 2/1988 | Hamaoka et al. |
| 4,762,707 | A | | 8/1988 | Jansen et al. |
| 4,828,991 | A | | 5/1989 | Hanna et al. |
| 4,952,394 | A | | 8/1990 | Senter |
| 4,975,278 | A | | 12/1990 | Senter et al. |
| 4,997,762 | A | | 3/1991 | Hanna et al. |
| 5,019,368 | A | | 5/1991 | Epstein et al. |
| 5,047,507 | A | | 9/1991 | Buchegger et al. |
| 5,055,404 | A | | 10/1991 | Ueda et al. |
| 5,162,504 | A | | 11/1992 | Horoszewicz |
| 5,474,755 | A | | 12/1995 | Hanna et al. |
| 5,489,525 | A | | 2/1996 | Pastan |
| 5,495,002 | A | | 2/1996 | Kobrin et al. |
| 5,614,373 | A | | 3/1997 | Stahel |
| 5,632,990 | A | | 5/1997 | Bagshawe et al. |
| 5,639,621 | A | | 6/1997 | Bosslet et al. |
| 5,639,656 | A | | 6/1997 | Wright |
| 5,670,151 | A | | 9/1997 | Larrick et al. |
| 6,207,805 | B1 | * | 3/2001 | Weiner et al. |

FOREIGN PATENT DOCUMENTS

| EP | 0268279 | 5/1988 |
|---|---|---|
| WO | WO9735616 | 10/1997 |
| WO | WO 9803873 | 1/1998 |
| WO | WO9639185 | 12/1998 |

OTHER PUBLICATIONS

Rudikoff et al., Proc. Natl. Acad. Sci. USA 79:1979–83, 1982.*

Bamias et al., Monoclonal antibodies in oncology: in–vivo targeting for immunoscintigraphy and therapy of human malignancies, in Monoclonal Antibodies, Production, Engineering and Clinical Application, ed. M. A. Ritter and H. M. Ladyman, Cambridge University Press, p. 222–46 (1995)—published sufficiently before filing date that the month is not an issue.

Scheinberg et al., Therapeutical Applications of Monoclonal Antibodies for Human Disease, in Monoclonal Antibodies: Principals and Applications, J.R. Birch and E. S. Lennox eds., Wiley–Liss p. 45–105, (1995)—published sufficiently before filing date such that the month is not an issue.

Ladyman et al., Production of monoclonal antibodies, in Monoclonal Antibodies, Production, Engineering and Clinical Application, ed. M. A. Ritter and H. M. Ladyman, Cambridge University Press, p. 9–33 (1995)—published sufficiently before filing date the month is not an issue.

Cannon et al., Immunoconjugates in Drug Delivery Systems, in Targeted Therapeutic Systems, P. Tyle and B. P. Ram eds., p. 121–139 (1990) published sufficiently before filing date such that the month is not an issue.

Mitra et al., Drug–Immunoglobulin Conjugates as Targeted Therapeutic Systems, in Targeted Therapeutic Systems, P. Tyle and B. P. Ram eds., p. 141–187 (1990) published sufficiently before filing date such that the month is not an issue.

S. Ramakrishnan, Current Status of Antibody–Toxin Conjugates for Tumor Therapy, in Targeted Therapeutic Systems, P. Tyle and B. P. Ram eds., p. 189–213 (1990)—published sufficiently before filing date such that the month is not an issue.

Katzenwadel Arndt et al., "Production and characterization of bispecific antibody with specificity for the CD3 complex and the prostate specific antigen" *Dialog Information Services, file 55, BIOSIS, Dialog accession No. 10918942, BIOSIS accession No. 199799540087,* Urological Research 25 (1): p 95 1997.

(List continued on next page.)

Primary Examiner—Sheela Huff
Assistant Examiner—Larry R. Helms
(74) Attorney, Agent, or Firm—Michael Best & Friedrich LLP; Teresa J. Welch

(57) ABSTRACT

Disclosed is an antibody that binds to a protein found on normal and cancerous prostate cells, but not found on nonprostate cells and a hybridoma that produces the antibody to the prostate-specific protein. Also disclosed are antibodies conjugated to labels or cytotoxic moieties.

28 Claims, 6 Drawing Sheets

OTHER PUBLICATIONS

Katzenwadel Arndt et al., "Production of a bispecific antibody with specificity for the CD3 complex and the prostate specific antigen as a possible tool for prostate cancer therapy" *Dialog Information Services, File 55, BIOSIS, Dialog accession No. 11326355, BIOSIS accession No. 199800107687,* Tumor biology 18 (Suppl. 2). P 18 Sep., 1997.

Philipp Holliger et al., "Retargeting serum immunog lobulin with bispecific diabodies" *Nature Biotechnology* vol. 15, Jul. 1997, p. 632–p. 636.

Bart–Jan Kroesen et al., "Bispecific Monoclonal Antibodies for Intravenous Treatment of Carcinoma Patients: Immunobiologic Aspects" *Journal of Hematotherapy ,*vol. 4, 1995, p. 409–p. 414.

Brian K. Link et al., "Production and Characterization of aBispecific IgGCapable of In ducing T–Cell–MediatedLysis of Malignant B Cells" *Blood,* vol. 81, No. 12, Jun. 1993, p. 3343—p. 3349.

Paul, Fundamental Immunology, Chapter 8, p 242, 1993.*

Sevier et al., Clin Chem 27:1797–1806, 1981.*

Seaver Genetic Engineering News, 14, pp. 10 and 21, 1994.*

* cited by examiner

PROSTATE CELL SURFACE ANTIGEN-SPECIFIC ANTIBODIES

CROSS-REFERENCE TO RELATED APPLICATION

This application is a continuation of U.S. Ser. No. 09/104,717, filed Jun. 25, 1998, issued as U.S. Pat. No. 6,207,805, which is a continuation-in-part of U.S. Ser. No. 08/896,447, filed Jul. 18, 1997 (abandoned).

FIELD OF THE INVENTION

The present invention relates to the field of monoclonal antibodies and their use in therapeutic applications. More particularly, bispecific antibodies have binding specificity for a prostate tissue marker and also binding specificity for CD3 antigen present on the surface of T lymphocytes.

BACKGROUND OF THE INVENTION

Prostatic cancer is a highly intractable disease which affects an increasing number of men, and now has surpassed lung cancer as the most frequently diagnosed cancer in men in the United States. Prostatic cancer is often curable if the tumor is confined to a small region of the gland and found at an early stage, and is destroyed by radiation or surgically removed in its entirety. Unfortunately, a great many prostatic cancers have already infiltrated surrounding tissue or have metastasized to remote sites, frequently the bone marrow, before initial detection. In this instance, radiation and other therapies may be more palliative than curative.

Once it was recognized how androgen dependent both normal development of prostatic cells and tumor growth were, androgen deprivation therapy appeared to offer a systemic mode of treatment. In fact, a dramatic remission in symptoms and tumor regression are observed in instances of castration or hormonal drug suppression, for which Charles Huggins won the Nobel Prize in 1966. However, the effects of androgen deprivation were temporary, and the cancers soon relapse with emergence of a new androgen independent cell type, which is unusually aggressive and resistant to all treatment modalities. In such instances, it is only the relatively slow progression of the disease in older patients and the intervention of other morbid processes, that permitted such patients to escape the inevitable outcome of the cancer. For a general review of issues in conventional treatment of prostate cancer, see "Prostate Cancer Working Group", Coffey, D. S., Chair, Cancer Res., 51: 1498 (1991).

Androgen deprivation is a useful therapy. Among the androgen suppressive drugs licensed by the FDA, are Stilphostrol, which is a phosphorylated nonsteroidal estrogen, and Lupron, a synthetic nonapeptide analog of GnRH. The relapse of temporary remission and emergence of androgen independent malignant cells is variable, and hormonal therapy offers many patients sustained relief for a time. It is not understood how the tumor cells overcome their androgen dependence, or if they do, since it has not been ruled out that, at least in some instances, the androgen independent cells arise from a different precancerous clone.

Nevertheless, new treatments are clearly needed. In the last few years, there has been a significant trend towards detection of prostate cancer more frequently and at earlier stages, brought about largely by the availability of more sensitive and accurate tests for the quantitation of Prostate Specific Antigen (PSA). Concomitantly, more is known about the molecular biology of prostatic tumor expression, although how these molecular discoveries can be translated into effective therapies is not clear. For example, the androgen dependence of the early malignant cells focusses attention on the AR gene and the SRD5A2 gene. Abnormal gene expression can result from gene amplification (AR) leading to altered expression, and from genetic polymorphisms (SDR5A2) associated with high risk individuals.

Karp, et al., Cancer Res., 56: 5547 (1996) describes a number of potential therapies based on some of the molecular observations. For example, targeting antiandrogen/ antiestrogen mechanisms with inhibitors of steroid 5alpha-reductase (Finansteride, etc., or steroid aromatise (Exemestane, etc.) may offer therapeutic possibilities. Also, drugs that suppress cellular proliferation, such as E-Cadherin mimetics, PD 153035 (through EGF receptor interaction), or Fluasterone (inhibition of nucleotide synthesis), may be effective where the molecular abnormality in a given tumor is diagnosed.

Monoclonal antibodies have been used in oncology as both diagnostic tools and therapeutic adjuncts. Unconjugated antibodies have been used in patients with acute leukemias (see more recent review). An antiganglioside monoclonal antibody has been used in some patients with melanomas to some advantage (see Houghton, et al., 85: 1242 (1985)). For conjugated antibodies, monoclonals bearing radionuclides have been evaluated. $^{131}$I and $^{90}$Y have been most extensively studied, although these are associated with some toxicity. Other antibody conjugates include biologic toxins (such as ricin, S. exotoxin, etc.) and chemotherapeutic drugs (such as methotrexate, or Doxorubicin).

A number of prostate-reactive antibodies have been produced and evaluated to various degrees. The most extensively studied antibody is designated 7E11 and reacts with PSMA. Radiolabelled 7E11 reacts specifically with prostate cancer cells, and has proven useful as a diagnostic agent in patients with occult recurrence of prostate cancer, as described in Kahn, et al., J. Urol., 152: 1490 (1994), and elsewhere. The use of this antibody (7E11-C5.3) in phase I clinical trials, labelled with 111In, is discussed in Monoclonal Antibodies 2: Applications in Clinical Oncology, ed. A. A. Epenetos, Chap. 32, Chapman & Hall Medical: 1993.

This antibody, however, has a number of limitations. It recognizes an intracellular rather than a surface epitope, thus having limited value in targeting viable cells. Thus, there exists a great need for monoclonal antibodies which have the desired specificity, and target epitopes of stably expressed antigen molecules on the surface of the target tumor cell.

The immune mechanisms leading to destruction of target tumor cells are partially understood. A population of cytolytic T cells have been identified which carry the CD8+ antigenic determinant on their surfaces. These cells require CD4+ helper lymphocytes for activation, which is a complex event mediated by antigen processing and presentation in association with the major histocompatibility complexes. Antigen processing assures that only cells targeted to the tumor antigens will be activated.

Monoclonal antibodies directed to various markers on subpopulations of T lymphocytes have been used to activate immune effector cells. OKT3 antibody administered by injection, for example, meets with CD3, and can cause a whole array of immune effects including IL-2, TNF-alpha, and IL-6 release, tissue damage, and either activation or suppression of T cell activity. More recently, OKT3 specificity has been combined with a antitumor specificity in a bispecific antibody. Link, et al., Blood, 81: 3343 (1993) showed that a bispecific antibody having one arm of OKT3 and the other arm directed to a B-cell malignant antigen was able to induce cytotoxicity of target tumor cells. Interestingly, the T-cell activation was without regard to the natural specificity of the T cell, and required the presence of the tumor cells. Thus, in the simultaneous binding of tumor cell and effector cell by the same antibody, the T cells are effectively recruited from the general T cell population, and retargeted to destroy the tumor cells.

It has also been shown by Weiner, Int. J. Cancer, Supplement 7, 63 (1992) that the action of the bispecific antibody is enhanced by coadministration of IL-2, so that combinational therapy resulted in management of a 100 to 1000 times greater tumor load than with the anti-tumor monoclonal antibody alone. Alternatively, the co-stimulus observed in the use of the bispecific antibody may be provided through binding of the Fc domain of the antibody to the Fc monocyte receptor, which in turn provide the co-stimulus, possibly through binding of the B7 family of membrane proteins to CD28. Preactivation ex vivo of cytotoxic T cells with co-administration of bispecific F(ab') has also been reported (Mezzanzanice, et al., Cancer Res., 51:5716 (1991).

SUMMARY OF THE INVENTION

The present invention utilizes a selection method designed to obtain monoclonal antibodies of very high specificity to particular tumor antigens, or to antigenic determinants shared by a single differentiated tissue type. It is also an objective to produce monoclonal antibodies which favor an externally disposed, stable, nonshed antigen. One problem with monoclonal antibodies raised to cell extracts derived from and screened against only one tumor or cell line, is their tendency to cross-react, however slightly, with vital non-tumor tissues. Many of the side-effects observed in immunotherapy are attributable to the nonspecific interaction of the antibody or antibody-toxin/drug/radionuclide conjugate with normal non-target cells, causing an associated toxicity. It is therefore an important object of this invention to provide an antibody of sufficient specificity that side-effects are minimized and limited to minor symptoms, or avoided.

Thus, in selecting an antibody specific for a common antigenic determinant displayed on the cell surface of cancers of a defined cell type, a mixture of cells is prepared, the mixture comprising cells from individual cell lines derived from a plurality of cancer cells of defined tissue type. This mixture of whole cells is then injected into a laboratory animal such as a mouse, according to a conventional immunization protocol to immunize the animal with the heterologous human tumor cells. Reactive B cells are then harvested from the animal, preferably the disrupted spleens, and fused with myeloma cells to form hybridomas. By maintaining the cell density below a critical level in which a statistical distribution function predicts one or two hybridomas per well, the likelihood of obtaining isolated single hybridomas was improved.

After cloning and outgrowth, supernatant medium containing the secreted monoclonal antibodies was removed. The screenings were then carried out, first, by contacting the mixture of cancer cells of the defined tissue, and a mixture of cancer cells of a different tissue type, with the monoclonal antibody under conditions conducive to binding of the antibody to cells displaying the target antigenic determinant. A fluorescent dye that recognizes the antibody is then added and the cells are then evaluated in a flow cytometer to determine which cells have detectable dye and which do not. The cell types are distinguished by a log scale of emission light intensity. Thus, the cells are ranked into a first class having labelled antibody bound to the surfaces thereof and into a second class having no labelled antibody bound, thereby showing a bimodal distribution of cells in flow cytometry.

The second screen involves further screening tests on the cells showing a bimodal distribution in which individual cells of prostate cancer and other cancer origin are labelled with the monoclonal antibody. Thus, each cancer cell type is individually tested with the labelled antibody to identify antibody with binding specificity for the cancer cells derived from the tissue of interest. Those antibodies which demonstrate unambiguous reactivity with prostate cancer-derived cells and no reactivity with nonprostate-derived cells are further tested. The cancer tissue types for which this method is intended in its therapeutic application include all those derived or arising from body organs unessential for viability such as ovary, breast, certain endocrine glands (thyroid), testicle, as well as prostate.

The third screening test is performed upon the monoclonal antibodies passing both the first and second screen, and involves determining the binding specificity of the labelled antibody for tissue sections derived from a plurality of cancers of defined cell type, together with controls of normal tissue sections from nonhomologous tissue.

In a variation of the above method involving the production of monoclonal antibodies specific for prostate tissue, the steps set forth therein are reproduced, with the exception that the initial immunization is carried out by preparing a whole cell suspended mixture of cells from cell lines derived from a plurality of prostatic tumors, proceeding through the next steps to grow out the hybridomas, but then performing the first screening test upon a mixture of the tumor cells contained in the inoculum and cells from cell lines not of prostate origin, after incubation with the labelled antibody. This variation in procedure does not screen against monoclonal antibodies reacting with both normal prostate and prostatic tumor cells, while not recognizing the nonprostate cells.

The invention herein encompasses the monoclonal antibodies obtained by the above disclosed methods, and also various diagnostic and therapeutic reagents made from them. Particularly useful are antibody conjugates in which a reporter molecule or detectable label is chemically conjugated to the antibody or an antibody fragment which retains the antigen binding characteristics and specificity of the originally isolated antibody. These reporters may be direct, such as a radioactive isotope or dye, or indirect, such as an enzyme, where the enzyme subsequently acts on a substrate to produce a detectable signal. In diagnostics, the reagents of the present invention will have especial efficacy in evaluating histologic sections and in immunoscintigraphy.

In therapeutic application in which the eradication of tumor cells is sought, the same antibodies will be efficacious, but with different conjugated moieties which are adapted for inducing cell death of the tumor cell to which they bind. The cytotoxic moieties may include a radionuclide, a chemotherapeutic drug, or a biologic toxin. In diagnostics application, tumor cells of unessential organs or tissue types widely distributed in the body may be used in the immunization, and then screened according to the present method. The monoclonals obtained cannot be used for therapeutic purposes, since normal tissue of the same type would be destroyed. However, they are useful as reagents in diagnostics, as in the tissue section illustrated in FIG. 4.

Applicants have also found that a bispecific construct which binds two antigens has cytotoxic activity against a tumor cell in the presence of one or more effector cells. The construct contains one or more polypeptides and is characterized in having a first binding domain having binding specificity for an antigenic determinant expressed on the surface of malignant and normal cells of defined nonessential animal tissue type, and a second binding domain having binding specificity for an antigenic determinant expressed on the surface of a defined class of immune effector cells such as monocyles, T-cells or NK cells. Antigenic determinants of tissue specific type include, for example, the determinant recognized by the 5E10 monoclonal antibody specific for prostate tissue. Other nonessential tissues having tissue specific determinants for which monoclonal antibodies may be isolated by the method of the present invention, include the thymus, thyroid, mammary gland, testes, ovaries, etc. Monoclonal antibodies specific for lymphocyte markers may be directed against CD3 (such as the commercially available OKT3), CD4, CD8, CD16, and CD28, CD32 and CD64.

Finally, in a still further embodiment of the present invention, a hybrid-hybridoma cell line is provided by first fusing an OKT3 secreting cell (ATCC Accession No. CRL 8001) with a 5E10 prostate tissue specific monoclonal antibody secreting cell, and growing out the fusion hybrid in a selective medium. The resulting hybrid-hybridoma cell line secretes monoclonal OKT3 antibody, 5E10 antibody, and a bispecific antibody having the combined specificity of OKT3 on one antibody arm, and 5E10 specificity on the other antibody arm.

DETAILED DESCRIPTION OF THE PREFERRED EMBODIMENT

Figure 1:
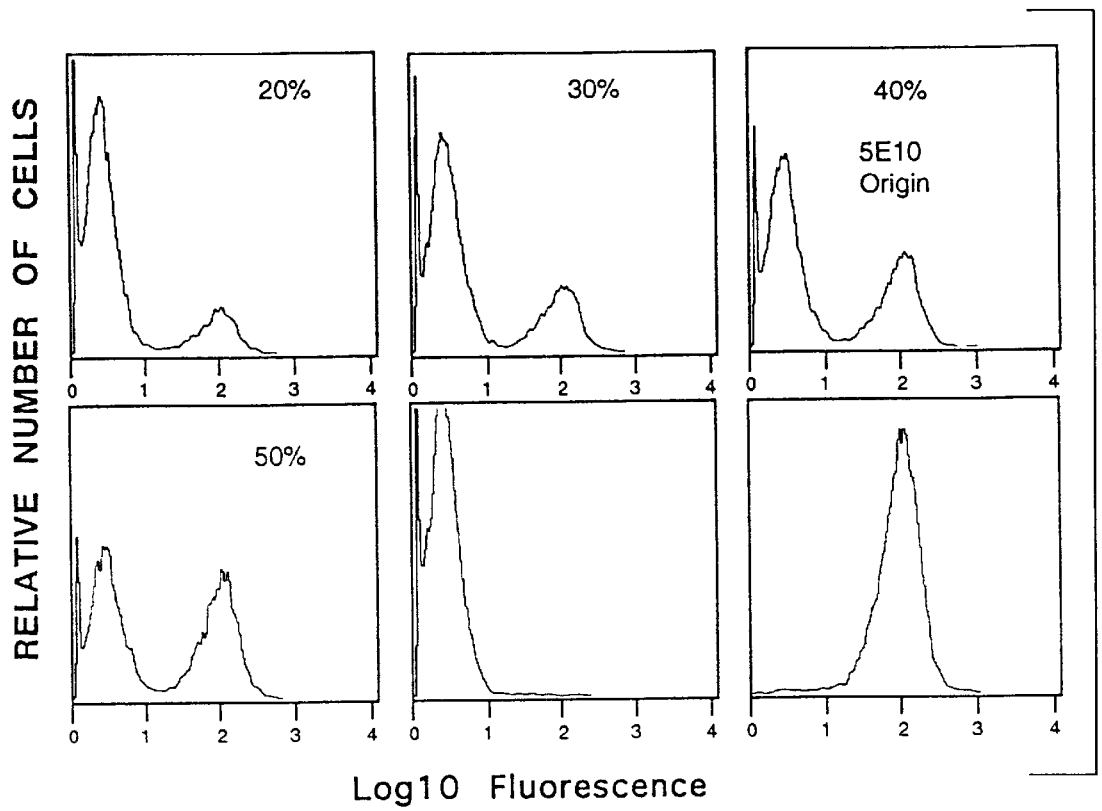
FIG. 1 is a rectilinear plot of cell numbers versus log 10 fluorescence showing flow cytometric analysis of surface expression by mixture of prostate and non-prostate cell lines after incubation with primary hybridoma supernatants. Bound antibodies were detected with PE-labeled goat antibodies to mouse Ig. Hybridomas with bimodal distribution of reactivity were selected for further evaluation.
Figure 2:
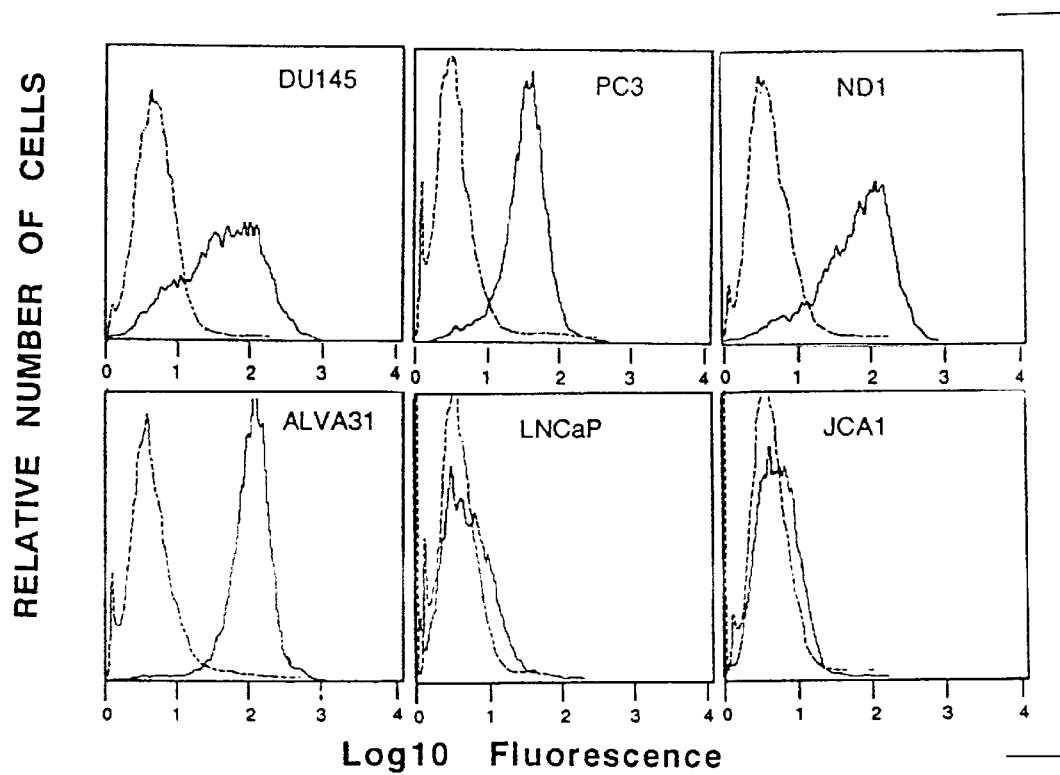
FIG. 2 is a rectilinear plot of cell numbers versus log 10 fluorescence showing flow cytometric analysis of 5E10 expression by human prostatic carcinoma cell lines. Bound monoclonal antibodies were detected with PE-labeled goat antibodies to mouse Ig. The dotted line represents control with irrelevant mouse IgG1; the solid line represents 5E10 expression.

The basic strategy in developing the present monoclonal antibodies is to maximize the likelihood of selecting an antibody having specificity for a antigenic determinant common to all or substantially all of the tumors derived from a particular tissue type. Pursuant to this strategy, a plurality of at least two and up to six to eight individual cell lines derived from tumors are grown up. The cells are washed, concentrated to a total cell density of about $10^7$ cells/ml in conventional media and injected into test animals, e.g. mice. This protocol is repeated once prior to harvest of spleens for recovery of immune B cells.

The simultaneous presentation of all the cell line antigens appears to result in the early emergence of clones secreting antibody with a specificity common to all cell lines. The alternative would be to immunize with a first cell line, and then boost with the different cell lines, in the hope that successive presentation of the common antigenic determinant would cause expansion of that clone over expression of those unique to the individual cell line (which would be presented to the immune system but once). This lengthy and laborious approach is unnecessary, as Applicants have discovered that simultaneous inoculation of all the chosen cell lines results in emergence of monoclonal antibody producing clones with specificity to a common antigen within two to three immunization events.

The term "derived" as it applies herein means the cells obtained by subculture of tumors isolated from patients. It also applies to cell lines established from non-solid tumors of the lymphatic system. The techniques for routine subculture of tumor cells are well known in the art, and include the use of growth factors, nutrients, support matrices, and hormones, as required for the particular tissue type. The techniques for immunization of experimental animals and subsequent cell fusion of splenic B cells to produce hybridomas, and their subsequent culture are conventional. The basic protocol utilized in the practice of the present invention is set forth in detail in *Current Protocols in Immunology*, vol. 1, J. E. Coligan, et al., eds., John Wiley & Sons: 1991 hereby incorporated by reference.

It is important in applying these protocols to the isolation of hybridomas according to the present invention, that a proper dilution of fused cells occurs, so that a substantial number of wells in the 96 well trays contain 1–2 clones, and not more. At dilutions sufficiently great to attain this objective, some 6 to 12 percent of wells will contain 0 clones. In the experiment from which the clone 5E10 was identified, some 20,000 cells were distributed in 960 plate wells.

Screening by flow cytometry has several key advantages. First, it is important that a stable cell surface antigen be identified. As indicated above, the 7E11 antibody directed to PSMA, and other tumor specific markers are not cell surface oriented. By selecting only those antibodies that bind whole cells, the likelihood of choosing a stable surface component antigen is enhanced. The term "stable" means in the context of antibody/cellular interactions, that the target molecule is preferably a constitutive cell membrane glycoprotein integral to the structure and integrity of the membrane, and not a transient resident of the cell which is shed, displaced, or antigenically modified during the cell cycle.

A second advantage to screening by flow cytometry, is that the bimodal profile indicates that some cells bind the fluorophore labelled antibody and not others, which is a threshold indication of specificity. If only a single fluorescent peak is observed, this means that some antigen common to both the tumor cells and the non-prostate cells has been identified by the antibody. Two peaks mean that either one or more subsets of tumor cells have a unique antigen, one or more subsets of tumor cells but not all share an antigen with the non-tumor cells, or that the tumor cells have an antigen not shared by normal cells. Another advantage of this method of preselection is that the techniques of labelling cells and preparing them for flow cytometry are well known, and may be carried out routinely.

In the case of prostate cancer therapy, it is not important if the monoclonal antibody does not distinguish between normal prostate and cancerous prostate cells. In many cases where remote imaging diagnosis or immunotherapy is indicated, the prostate gland has already been removed. The prostate is unessential in the sense that its absence per se is not life threatening. The 5E10 antibody disclosed in the Example is specific for prostate-derived cells generally, and recognizes a prostate marker common to both normal and cancerous cells. Applicants have correctly surmised that an antigen common to both cancerous and noncancerous prostate cells, and specific to that differentiated cell type would be readily recognized by a xenotypic immune system. Although the methods of the present invention can be applied to the isolation of hybridomas secreting antibodies reactive to tumor specific antigens for a given cell type, the preferred embodiment herein utilizes the method to identify cell type specific antigens which may be found on both normal and cancerous tissue derived from the same cell type. This technique may be used to identify any monoclonal antibody specific for an antigenic determinant common to a normal cell type and its tumor counterpart, for an organic nonessential for viability of the animal from which it was obtained other than the prostate, ovary, breast, testicle, and thyroid are examples of such organs.

In the use of the antibodies of the invention for diagnostic purposes, the antibody must be labelled. Any conventional means of labelling antibodies which does not interfere with binding specificity may be employed. Many of the techniques for labelling and for formatting diagnostic imaging assays are set forth in *Monoclonal Antibodies: Principles and Applications*, J. R. Birch, et al., eds., Wiley-Liss: 1995, hereby incorporated by reference, and references cited therein.

In the use of the antibodies for therapeutic purposes, the conjugation of antibody with radionuclides, enzymes, biologic toxins, and chemotherapeutic drugs is well known in the art. Some of the more current strategies for molecular linkers are reviewed in Reisfeld, et al., *Antibodies as Therapeutic Agents and Carriers for Drugs*, Permagon Press: 1990, and references cited therein. The mycotoxins are particularly preferred in therapeutic actions, since some of them have an extremely high toxicity to cells, can be linked reversibly to the antibody through an adoptive sulfhydryl bond, and as free molecules do not have independent cell binding receptors. Biologic toxins useful in the present invention include ricin, abrin, amantin, trichosanthin, and restrictocin. Enzymes that can be successfully localized at the tumor site include carboxypeptidase, alkaline phosphatase, thymidine kinase, as described in *Monoclonal Antibodies: Production, Engineering, and Clinical Application*, M. A. Ritter, et al., eds., Cambridge University Press: 1995. Molecular conjugation of radionuclides and therapeutic protocols are described in detail in *Therapeutic Monoclonal Antibodies*, C. Borrebaeck, et al., eds., M Stockton Press: 1990.

Bispecific antibodies have been utilized in a variety of therapeutic applications. U.S. Pat. No. 5,601,819 (Wong) discloses the use of a combinational CD3, and CD28 or interleukin 2 receptor bispecific antibody to selectively cause proliferation and destruction of specific T cell subsets. Belani, et al. showed that bispecific IgG functions in a B cell lymphoma model to retarget the specificity of T cells in low dose, and to cause nonspecific T cell activation with systemic cytokine production at higher doses. It was found that bsF(ab')2 was also capable of retargeting T-cell mediated lysis by activated T cells. Thus, in many applications portions of antibodies, such as enzyme digested fragments, will mediate the effects otherwise observed for the intact antibody. These fragments necessarily contain the complementarity determining regions (CDRs) of the variable light and heavy chain antibody domains, and may be integrated with other protein fragments to form a bispecific antigen binding protein construct. This construct will minimally contain the CDRs including the interspersed constant framework beta sheet portions. These regions are easily identified following routine cloning and sequencing procedures, as disclosed in U.S. Pat. Nos. 5,530,101 and 5,585,089, hereby incorporated by reference. Cloning is facilitated by PCR primers complementary to conserved sequences flaking the functional variable regions.

Useful bispecific antibodies combining a CDR specific for an effector cell and the CDR for a tissue specific antigen may also be humanized, either by replacing the light and heavy chain constant regions of the murine antibody with their human counterparts, or by grafting the CDRs onto a human antibody. Methods for carrying out these procedures are contained in U.S. Pat. Nos. 5,530,101 and 5,585,089. The immune construct of the present invention may also be bispecific single chain antibodies, which are typically recombinant polypeptides consisting of a variable light chain portion covalently attached through a linker molecule to the corresponding variable heavy chain portion, as disclosed in U.S. Pat. Nos. 5,455,030, 5,260,203, and 4,496,778, hereby incorporated by reference. A more complex construct for a single chain bispecific antibody also containing an Fc portion is provided in detail in U.S. Pat. No. 5,637,481. The principal advantage of constructs of this type is that only one species of antibody is produced, rather than three separate antibody types in the fused cell hybrid-hybridoma, which require further purification.

Other methods can be utilized in producing bispecific antibodies. Chemical heteroconjugates can be created by the chemical linking of either intact antibodies or antibody fragments of different specificities. Karpovsky et al., Production of Target-Specific Effector Cells Using Hetero-Cross-Linked Aggregates Containing Anti-Target Cell and Anti-Fc Gamma Receptor Antibodies, *J. Exp. Med.* 160: 1686–1701 (1984). However, these heteroconjugates are difficult to make in a reproducible manner and are at least twice as large as normal monoclonal antibodies. Bispecific antibodies may also be created by disulfide exchange, which involves enzymatic cleavage and reassociation of the antibody fragments. Glennie et al., Preparation and Performance of Bispecific F(ab')$_2$ Antibody Containing Thioether Linked Fab' Fragments, *J. Immunol.* 139: 2367–2375 (1987). Another method is the creation of F(ab')$_2$ connected via a shortened Fc to the leucine zipper region of the transcription factors Fos and Jun. Kostelny et al., Formation of a Bispecific Monoclonal Antibody by the Use of Leucine Zippers, *J. Immunol.* 148: 1547–53 (1992).

Bispecific antibodies are also produced by hybrid-hybridomas. Hybrid-hybridomas are created by fusing two hybridoma cell lines together so that the resulting hybrid-hybridoma contains two productive light chain alleles. Hybrid-hybridomas secrete individual bispecific IgG molecules which are monovalent for each of the two distinct antigens recognized by antibodies produced by the parent hybridomas. However, hybrid-hybridomas produce both bispecific antibodies and monospecific antibodies for each of the two antigens recognized by the parent hybridomas. Further, light chain/heavy chain fidelity does not always occur. In all, there are 10 possible heavy and light chain combinations that could be produced by the hybrid-hybridoma cell line. Only one of these is the desired bispecific antibody. Some degree of purification of the bispecific component is therefore necessary prior to the use of such bispecific antibodies. A preferred method of purification is protein A immunoaffinity chromatography followed by HPLC purification.

Preferably, the anti-prostate bispecific antibody of the present invention has a first Fab portion specific for an antigenic determinant on target cells, most preferably, an Fab portion from an antibody produced by the cell line designated 5E10 which is specific for prostate cells. The second Fab fragment is specific for an antigenic determinant on an immune system effector cell, most preferably, the Fab portion is derived from OKT3. The Fab portions share a common Fc region. Most preferably, the bispecific antibodies are produced by a hybrid-hybridoma cell line formed by the fusion of a hybridoma cell line selected by the flow cytometric screening method of the present invention and a hybridoma which produces antibodies specific for antigens on immune system effector cells. Preferably the first hybridoma cell line is the cell line designated 5E10 having specificity for an antigen expressed on prostate cells and the ATCC Accession No. XXXXX. The second hybridoma cell line may be selected from the group of cell lines expressing antibodies specific for CD16, CD28 and CD3, preferably the cell line expressing OKT3 (ATCC CRL 8001). Most preferably, the bispecific antibodies are produced by the cell line having the ATCC Accession No. PTA-865, which was deposited on Oct. 29, 1999 at the American Type Culture Collection (ATCC), 10801 University Boulevard, Manassas, Va., 20110, under the terms of the Budapest Treaty.

CD3 binding by OKT3 or a bispecific antibody with one OKT3 variable region only partially activates the CTL. Additional co-stimulatory signals are required to fully activate the CTL so that it has cytolytic activity. An intact bispecific antibody has the ability to provide its own co-stimulatory signal, as disclosed in Weiner et al., *J. Immunol.*, 152:2385 (1994). The inventors hypothesize that the co-stimulatory activity is provided through the interaction of the Fc region of the bispecific antibody with the Fc receptor of circulating monocytes. The monocyte expresses members of the B7 family of co-stimulatory molecules at its cell surface. These B7 molecules bind to CD28 expressed by the CTL and cause co-stimulatory activation of the CTL. Therefore, the bispecific antibody actually may target both CTLs and monocytes to the tumor cell. This pathway also results in the localized release of cytokines at the site of the tumor which may contribute regression of both antigen positive and antigen negative tumors.

Other advantages of the present invention will be apparent from the Examples which follow.

EXAMPLE 1

Immunization and Fusion

Mice were immunized two times with a mixture of prostate tumor cell lines: primary cell lines: ALVA31, JCA1, ND1; metastatic cell lines: DU145, LNCaP, and PC3. Mice were injected with living cells in PBS, $12 \times 10^6$ cells per mouse ($2 \times 10^6$ of each cell line). Spleen was taken for fusion on fourth day after second immunization.

In two preliminary fusions, cells were seeded at 100,000 and 50,000 per well and it has been found that almost 100% of wells contained multiple clones which seemed to produce mixture of monoclonal antibodies (mAbs) reacted both with prostate and non-prostrated cell lines. Therefore, after third fusion, cells were seeded at 20,000 cells per well in 10 plates, i.e. 960 wells. Microscopic examination of wells revealed that 85 wells did not contain any clones (8.8%), 493 wells contained three or more clones (51.4%) and 382 wells contained 1–2 clones (39.8%), and the latters were analyzed by flow cytometry.

Flow Cytometric Screening

Step 1. The supernatants were added to a mixture of cells containing all 6 prostate cell limes used in immunization, and 6 non-prostate cell lines indicated in Table 1. Antibodies that reacted with some cells in this mixture but not all (i.e. those that gave a bimodal pattern of staining on the mixture of 12 cell lines, see FIG. 1) were selected for further evaluation. This approach excluded those monoclonal antibodies that recognized non-membrane surface proteins, or monoclonal antibodies that recognize an epitope that is not specific for the prostate cancer cells. Twenty-two wells (5.8%) with bimodal pattern of reactivity were identified on this step of screening.

Step 2. Hybridoma cells from selected 22 primary wells were transferred from 96-well plates to 24-well plates, cells were grown for several days and supernatants were screened for reactivity with each of the prostate and non-prostate cell lines individually (i.e. all 12 lines). Five hybridoma populations with preferential reactivity with prostate cell lines were selected on this step (see Table 1).

Step 3. The specificity of five selected hybridomas was further assessed on peripheral blood cells (T- and B-lymphocytes, monocytes, granulocytes, erythrocytes, and platelets), bone marrow cells, both hematopoietic cells and stromal fibroblasts, and on endothelial cells, both primary cultured cells (HUVEC) and endothelial cell lines ECV-304. All five hybridomas examined were found to be negative with analyzed cell types (Table 1).

Step 4. They hybridoma cells were cloned and reactivity of individual clones was again estimated on prostate and non-prostate cell lines, peripheral blood, bone marrow, and endothelial cells (Table 1).

Step 5. Reactivity of selected hybridoma clones was further evaluated by immunohistochemical staining of tissue samples. It was found that only the 5E10 hybridoma reacted with both benign and malignant prostate epithelium in 6 of 6 histological samples, and did not react with other tissues (Table 2). Immunohistochemical staining for 5E10 was performed on a variety of frozen tissue specimens using a standard labeled streptavidin-biotin method. Frozen sections were cut and fixed in cold acetone for 5 minuets. Sections were then covered with primary antiserum (5E10), incubated at room temperature for 1 hour, and rinsed. Sections were then covered with a secondary antibody using the LSAB II Lind AB (Dako Corp;, Carpinteria, Calif.) for 15 minutes at room temperature, rinsed, and then covered with LSAB II labeled Ab for 15 minutes at room temperature and rinsed. Sections were subsequently incubated with 0.05% DAB/0.1 M TRIS with 0.015% H202 to demonstrate signal of the primary antibody. A counter stain of 10% Harris Hematoxylin without acid for 1–2 minutes was used. Negative control slides were prepared by substituting normal mouse serum for the primary antibody (5E10). All rinses were performed using 1% BSA/PBS Buffer.

Several clones were identified and evaluated by flow cytometry for reactivity with each of the prostate and non-prostate cell lines individually (i.e. all 12 lines). The most attractive clone, designated 5E10, produced an IgG1 that recognized 4 of the 6 prostate cell lines (DU145, PC3, ND1 and ALVA31). It reacted with both benign and malignant prostate in 6 of 6 histologic samples of prostate cancer tissue. Reactivity was stronger with the malignant tissue. There was no reactivity of 5E10 with non-prostate tumor cell lines, peripheral blood mononuclear cells or bone marrow stromal cells. A large number of frozen normal tissues were obtained at autopsy of patients that died of other disorders. Very weak reactivity was noted with some adnexal structures in the skin, and with a small subpopulation of mesenchymal cells in the kidney. No reactivity was noted with other normal tissues. In addition, the 5E10 antigen is a membrane antigen, does not appear to be shed, and the epitope recognized by 5E10 is extracellular. Western blot analysis demonstrates the 5E10 antigen is a glycoprotein that has a molecular weight of ~115 Kd. Ongoing studies are exploring the nature of this antigen in more depth.

To determine whether 5E10 is transmembrane or phosphatidylinositol anchored membrane protein, cells were treated with phosphatidylinositol phospholipase C and then stained with 5E10 monoclonal antibody. It has been found that this treatment did not affect the surface expression of 5E10. Treatment of cell lysates with N-glycanase reduced the molecular weight from 115 kDa to 110 kDa. Subsequent digestion of the lysates with neuraminidase has further reduced molecular weight by 20 kDa.

Figure 3:
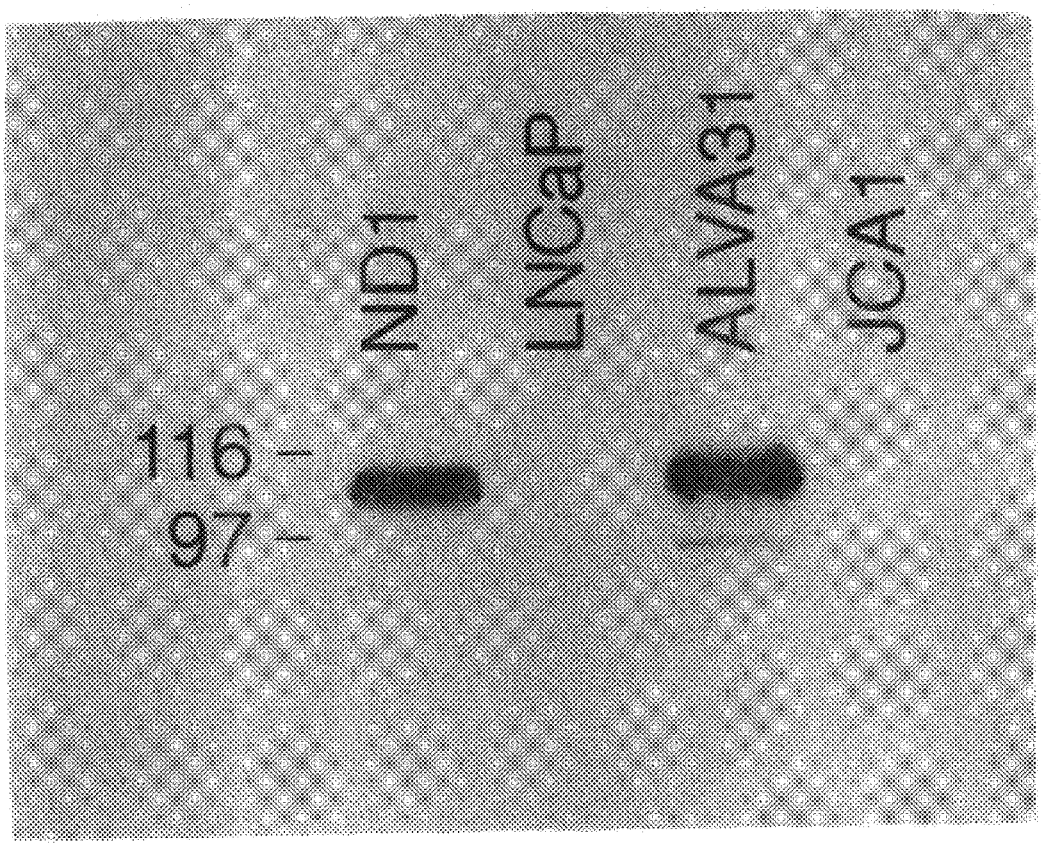
FIG. 3 is a western blot of 5E10 expression in prostate cell lines. Cellular protein lysates were resolved by 4–20% SDS-PAGE under reducing conditions, transferred to a nitrocellulose membrane, and detected by 5E10 monoclonal antibody.

Thus, 5E10 hybridoma produced IgG1 monoclonal antibody that recognized 4 of the 6 prostatic cancer cell lines, reacted with benign and malignant prostate and did not react with non-prostate tissues, peripheral blood cells, bone marrow hematopoietic and stromal fibroblast cells, and endothelial cells. In addition, it was found that the 5E10 antigen is a transmembrane glycoprotein which has a molecular weight of 110–115 kDa and contains N-linked oligosaccharides and sialic acid residues, as shown in FIG. 3, by western blot. In this figure, the form lanes corresponding to extracts of the cell lines individually react with 5E10 according to the reactivities shown in Table 1.

Figure 4:
FIG. 4 is a frozen section of prostate tissue showing the highly specific binding of the 5E10 antibody to the prostate epithelial cell by indirect immunofluorescence.

FIG. 4 further illustrates the specificity of the 5E10 antibody. Prostatic tissue sections were prepared by conventional frozen section, and reacted with the 5E10 antibody. Indirect fluorescence labelling clearly shows the specificity of the monoclonal antibody 5E10 for the epithelial cell surfaces. This figure also illustrates the efficacy of this technique as a diagnostic aid in identifying organ specific tissues or tumor cells derived or arising from such organ specific tissue.

TABLE 1

| | 1C2 (4 clones) | Hybridomas 1A7 (2 clones) | 5E10 (3 clones) | 5D4 (4 clones) | 2C9 (3 clones) |
|---|---|---|---|---|---|
| Targets 1/Prostate cell lines | | | | | |
| DU145 | + | + | + | + | – |
| PC3 | + | + | + | + | – |
| ND1 | + | + | + | + | – |
| LNCaP | – | + | – | + | + |
| ALVA31 | + | + | + | + | – |
| JCA1 | + | + | – | – | – |
| 2/Non-prostate cell lines | | | | | |
| A549 (Lung) | + | + | – | – | – |
| SKLU1 | – | – | – | – | – |

TABLE 1-continued

| | 1C2 (4 clones) | Hybridomas 1A7 (2 clones) | 5E10 (3 clones) | 5D4 (4 clones) | 2C9 (3 clones) |
|---|---|---|---|---|---|
| (Lung) 1072F (Renal) | – | – | – | – | – |
| UIR1 (Renal) | – | – | – | – | – |
| SKBR3 (Breast) | – | – | – | – | – |
| 5673 (Bladder) | – | – | – | – | – |
| 3/Peripheral blood cells: | | | | | |
| T- and B-lymphocytes monocytes granulocytes erythrocytes platelets 4/Bone marrow: | – | – | – | – | – |
| stromal fibroblasts and hematopoietic cells 5/Endothelial cells, | – | – | – | – | – |
| HUVEC and ECV-304 | – | – | – | – | – |

TABLE 2

IMMUNOHISTOCHEMICAL STAINING RESULTS WITH 5E10

| Tissue | # cases examined | staining result* |
|---|---|---|
| prostate* | | |
| benign | 8 | + |
| malignant | 7 | + |
| bladder | 3 | – |
| skeletal muscle | 5 | – |
| smooth muscle | 5 | – |
| lung | 4 | – |
| heart | 4 | – |
| stomach | 5 | – |
| colon | 5 | – |
| testis | 4 | – |
| spleen | 4 | – |
| skin | 3 | +/–(1) |
| nerve | 4 | – |
| kidney | 8 | – |
| liver | 5 | – |
| small bowel | 4 | – |
| adrenal | 4 | – |

*staining result:
+ positive staining
– no staining
(1)positive staining of skin is limited to select adnexal structures

EXAMPLE 2

Production of a 5E10×anti-CD3 BsAb

Figure 5:
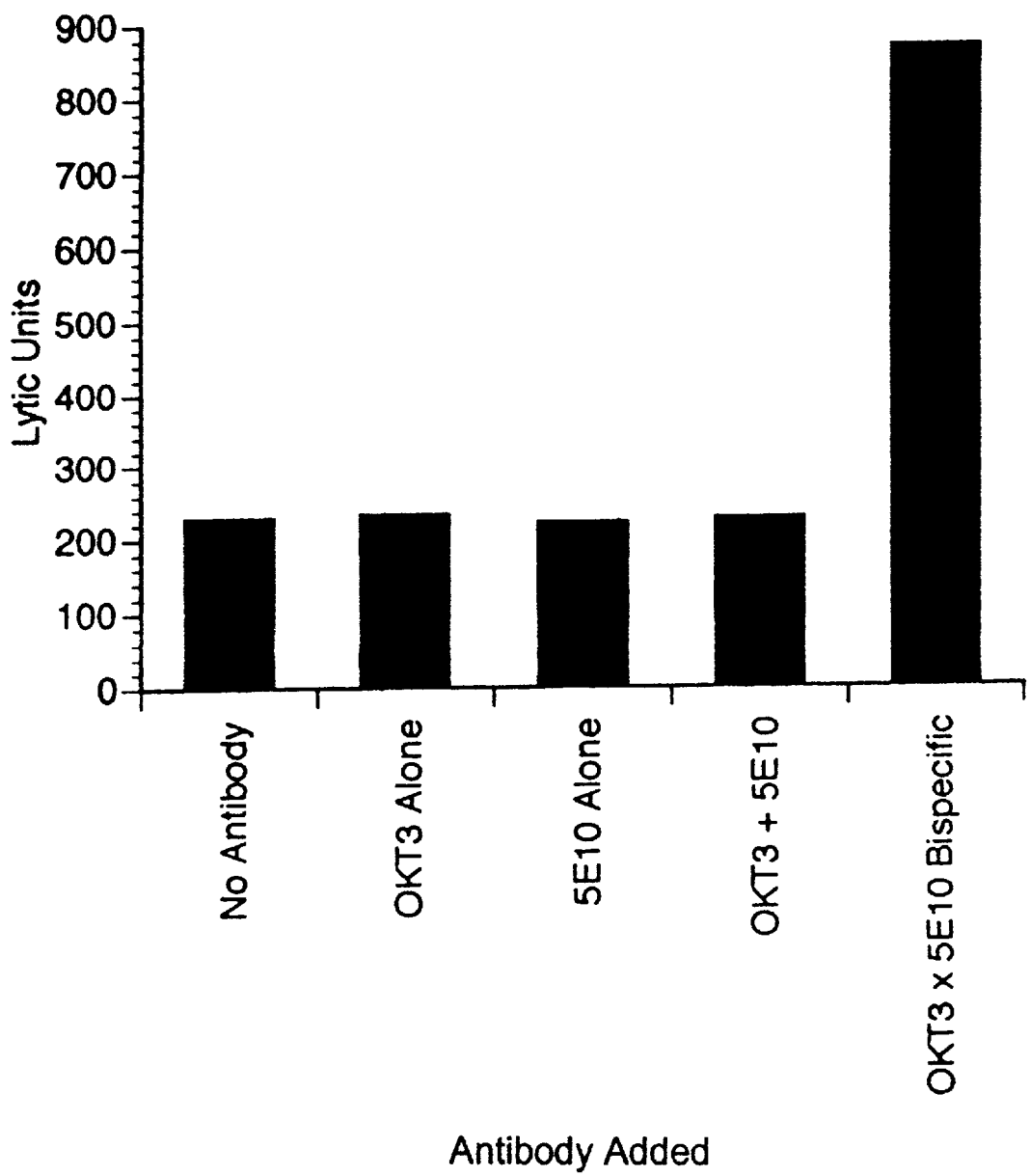
FIG. 5 is a bar graph comparing cell lysis of monospecific antibodies with the bispecific 5E10/OKT3 antibody.
Figure 6:
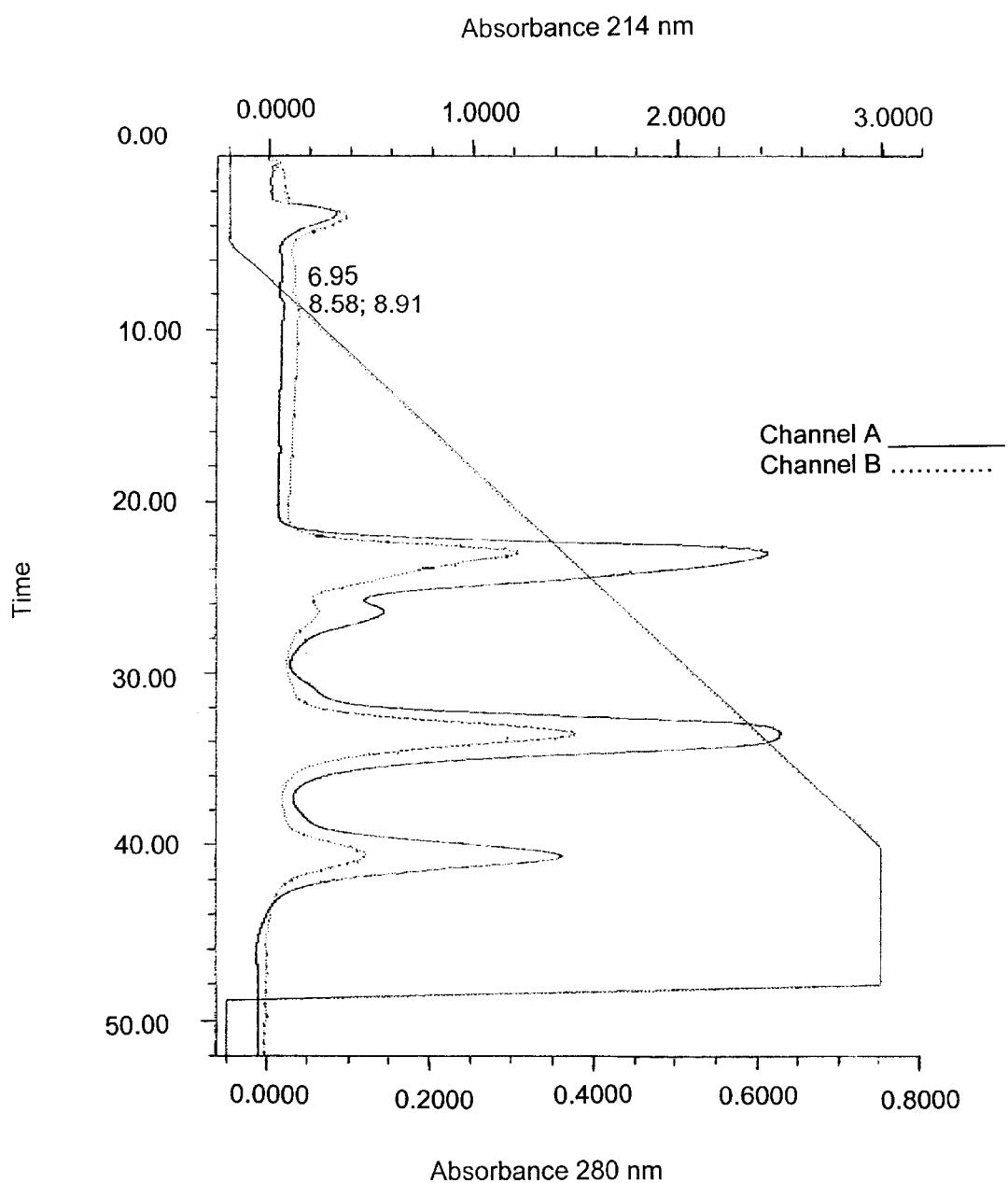
FIG. 6 is an HPLC plot showing the migratory position of each of the species of antibody secreted by the hybrid-hybridoma.

A hybrid-hybridoma capable of making a bispecific antibody was produced by fusing the hybridoma cells that secrete 5E10 with those that secrete OKT3 (FIG. 5). OKT3 is an IgG2a murine monoclonal antibody that reacts with the CD3 receptor on human T-cells. The cell line that produces OKT3 cell line was obtained from ATCC Accession No. CRL 8001. A variant of OKT3 was produced that is sensitive to Aminopterin and resistant to Neomycin. Hybrid-hybridomas were produced by the fusion of HAT resistant, neomycin sensitive 5E10 hybridomas and HAT sensitive, neomycin resistant OKT3-secreting hybridomas. Fused cells were plated in HAT-neomycin media to select for hybrid-hybridomas. The HAT in this media prevents the growth of unfused OKT3 cells and the neomycin will prevent the growth of unfused 5E10 cells. Thus, only hybrid-hybridomas containing genetic material from both parental hybridomas will survive. A panel of hybrid-hybridomas that produce BsAb were produced.

A two-step screening procedure was used to determine which hybrid-hybridomas are secreting BsAb. In the initial screen, hybrid-hybridoma supernatant was added separately to PC3 cells or Jurkat (CD3-expressing human T cell leukemia cells). Goat anti-mouse IgG-FITC was added after Washington detect the presence of bound antibody. Hybrid-hybridomas secreting antibody capable of binding to both PC3 and Jurkat cells were selected for further study.

A second screen was used to confirm bispecific reactivity by detecting the ability of BsAb-containing supernatant to induce the formation of PC3 and Jurkat cell aggregates. This assay has proven successful in our laboratory for the final selection of other BsAb secreting hybrid-hybridomas. PC3 cells were stained with supravital membrane dye DiO to stain cells green and Jurkat cells will be stained in a similar manner with the red dye DiI. PC3 and Jurkat cells were mixed together along with antibody (hybrid-hybridoma supernatant). Cells were evaluated by fluorescent microscopy and two-color flow cytometry.

Increased aggregate formation, as detected by red and green fluorescence, was seen when the hybrid-hybridoma supernatant contains functional BsAb capable of binding to both cell lines. The hybrid-hybridoma supernatant inducing the highest percent of aggregates (7.5% aggregates compared to 1.5% aggregates for control sample containing monospecific mAbs) was selected for further study. These results are similar to those seen in our successful development of a bispecific antibody for lymphoma.

The selected hybrid-hybridoma was subcloned by limiting dilution and bispecific reactivity confirmed. Large quantities of the bispecific antibody were produced. Antibody-containing supernatant was obtained from supernatant of mass culture of the hybrid-hybridoma. Affinity chromatography using staphylococcal protein A was used to obtain antibody produce from the supernatant. This antibody product was fractionated by HPLC, and the resulting antibody peaks screened for bispecific antibody activity.

Cytotoxicity assays

BsAb was evaluated for ability to mediate destruction of prostate cancer cells in vitro. Peripheral blood mononuclear cells from normal volunteers were used as effector cells. These were cultured in 50U recombinant IL-2 and 10 µg/ml purified OKT3 for 5 days. ALVA 31 cells were labelled with $^{51}$Cr by standard protocol and used as target cells. Effector cells and target cells were mixed at varying effector: target ratios, and BsAb or monospecific antibody added to each well at a final concentration of 1 µg/ml. Lysis induced by BsAb was compared to that induced by monospecific 5E10, monospecific OKT3 or a combination of both. The results, reported as lytic units (20% lysis), demonstrates the bispecific antibody retargets T-cell mediated lysis.

What is claimed is:

1. A purified monoclonal antibody having specificity to an antigenic determinant on the surface of normal and cancerous prostate-derived cells but not on the surface of non-prostatic tumor cells, peripheral blood cells, bone marrow hematopoietic and stromal fibroblast cells, or endothelial cells, wherein the antigenic determinant is a protein having a molecular weight of about 115 kDa as measured by SDS-polyacrylimide gel electrophoresis, wherein the prostate-derived cells are DU145 cells, ND1 cells, PC3 cells, or a combination thereof.

2. The antibody of claim 1, wherein the antibody is produced in the IgG1 class.

3. The monoclonal antibody of claim 1, wherein the prostate-derived cells are ND1 cells.

4. A reagent comprising a purified monoclonal antibody, or an antigen-binding fragment thereof, having specificity to an antigenic determinant on the surface of normal and cancerous prostate-derived cells but not on the surface of non-prostatic tumor cells, peripheral blood cells, bone marrow hematopoietic and stromal fibroblast cells, or endothelial cells, wherein the antigenic determinant is a protein having a molecular weight of about 115 kDa as measured by SDS-polyacrylimide gel electrophoresis, wherein the prostate-derived cells are DU145 cells, ND1 cells, PC3 cells, or a combination thereof.

5. The reagent of claim 2, wherein the antibody or antigen-binding fragment further comprises a detectable label stably conjugated thereto, the label selected from the group consisting of an enzyme, a radioisotope, and a dye molecule.

6. The reagent of claim 5 wherein said label is selected from the group consisting of $^{131}$I, $^{111}$In, $^{90}$Y, and $^{99}$Tc.

7. A reagent comprising a purified monoclonal antibody, or an antigen-binding fragment thereof, having specificity to an antigenic determinant on the surface of normal and cancerous prostate-derived cells but not on the surface of non-prostatic tumor cells, peripheral blood cells, bone marrow hematopoietic and stromal fibroblast cells, or endothelial cells, wherein the antigenic determinant is a protein having a molecular weight of about 115 kDa as measured by SDS-polyacrylimide gel electrophoresis, wherein the prostate-derived cells are DU145 cells, ND1 cells, PC3 cells, or a combination thereof, and a cytotoxic moiety conjugated thereto.

8. The reagent of claim 7, wherein the cytotoxic moiety is selected from the group consisting of a radionuclide, a chemotherapeutic drug, and a biologic toxin.

9. The reagent of claim 4, the reagent comprising an antigen binding fragment of the monoclonal antibody of claim 1.

10. The reagent of claim 9, wherein the antigen binding fragment is comprised in an antibody or antibody construct.

11. The reagent of claim 10, wherein the antibody or antibody construct is humanized.

12. The reagent of claim 11, wherein the humanized antibody or antibody construct comprises murine complementarity determining regions grafted onto a human antibody or antibody construct, wherein the murine complementarity determining regions specifically bind to the antigenic determinant of claim 1.

13. The reagent of claim 9, wherein the antibody or antibody construct is associated with at least one cytotoxic moiety selected from the group consisting of radionuclides, enzymes, biologic toxins and chemotherapeutic drugs.

14. The reagent of claim 13, wherein the cytotoxic moiety is a radionuclide.

15. The reagent of claim 14, wherein the radionuclide is selected from the group consisting of $^{90}$Y, $^{131}$I, $^{111}$In and $^{99}$Tc.

16. The monoclonal antibody of claim 1, wherein the cancerous prostate-derived cells are DU145.

17. The monoclonal antibody of claim 1, wherein the antibody does not bind LNCaP cells.

18. The monoclonal antibody of claim 1, wherein the prostate-derived cells are PC3 cells.

19. The monoclonal antibody of claim 17, wherein the prostate-derived cells are DU145 cells.

20. The monoclonal antibody of claim 17, wherein the prostate-derived cells are ND1 cells.

21. The monoclonal antibody of claim 17, wherein the prostate-derived cells are PC3 cells.

22. A purified monoclonal antibody having specificity to an antigenic determinant on the surface of normal and cancerous prostate-derived cells but not on the surface of non-prostatic tumor cells, peripheral blood cells, bone marrow hematopoietic and stromal fibroblast cells, or endothelial cells, wherein the antibody binds to DU145 cells, ND1 cells, and PC3 cells, and wherein the antibody does not bind to LNCaP cells.

23. The reagent of claim 4, wherein the prostate-derived cells are DU145 cells.

24. The reagent of claim 4, wherein the prostate-derived cells are ND1 cells.

25. The reagent of claim 4, wherein the prostate-derived cells are PC3 cells.

26. The reagent of claim 7, wherein the prostate-derived cells are DU145 cells.

27. The reagent of claim 7, wherein the prostate-derived cells are ND1 cells.

28. The reagent of claim 7, wherein the prostate-derived cells are PC3 cells.

* * * * *

UNITED STATES PATENT AND TRADEMARK OFFICE
CERTIFICATE OF CORRECTION

PATENT NO. : 6,512,096 B2
DATED : January 28, 2003
INVENTOR(S) : George J. Weiner, Oskar W. Rokhlin and Michael B. Cohen It is certified that error appears in the above-identified patent and that said Letters Patent is hereby corrected as shown below:

Column 14,
Line 22, "2" should read -- 4 --.

Signed and Sealed this

Thirteenth Day of July, 2004

JON W. DUDAS
*Acting Director of the United States Patent and Trademark Office*